US009008272B2

(12) United States Patent
Shu et al.

(10) Patent No.: US 9,008,272 B2
(45) Date of Patent: Apr. 14, 2015

(54) PRECISION MECHANICAL STRUCTURE OF AN ULTRA-HIGH-RESOLUTION SPECTROMETER FOR INELASTIC X-RAY SCATTERING INSTRUMENT

(75) Inventors: Deming Shu, Darian, IL (US); Yuri Shvydko, Lisle, IL (US); Stanislav A. Stoupin, Willowbrook, IL (US); Ruben Khachatryan, Plano, IL (US); Kurt A. Goetze, Geneva, IL (US); Timothy Roberts, Hobart, IN (US)

(73) Assignee: UChicago Argonne, LLC, Chicago, IL (US)

( * ) Notice: Subject to any disclaimer, the term of this patent is extended or adjusted under 35 U.S.C. 154(b) by 441 days.

(21) Appl. No.: 13/551,788

(22) Filed: Jul. 18, 2012

(65) Prior Publication Data

US 2014/0023180 A1 Jan. 23, 2014

(51) Int. Cl.

| | |
|---|---|
| ***G21K 1/06*** | (2006.01) |
| ***G01N 23/20*** | (2006.01) |
| ***G01N 23/207*** | (2006.01) |

(52) U.S. Cl.

CPC ..... *G01N 23/20025* (2013.01); *Y10T 29/49826* (2013.01); *G01N 23/2076* (2013.01)

(58) Field of Classification Search

USPC ..................................................... 378/85, 84

See application file for complete search history.

(56) References Cited

U.S. PATENT DOCUMENTS

| | | | | |
|---|---|---|---|---|
| 4,776,696 | A | 10/1988 | Hettrick et al. | |
| 5,526,903 | A | 6/1996 | Shu et al. | |
| 5,896,200 | A | 4/1999 | Shu | |
| 6,607,840 | B2 | 8/2003 | Shu et al. | |
| 6,982,792 | B1 * | 1/2006 | Woollam et al. | 356/369 |
| 6,984,335 | B2 | 1/2006 | Shu et al. | |
| 7,331,714 | B2 | 2/2008 | Shu et al. | |
| 8,089,199 | B2 | 1/2012 | Shu et al. | |
| 2003/0202186 | A1 | 10/2003 | Chan et al. | |
| 2009/0026569 | A1 | 1/2009 | Dongliang et al. | |
| 2011/0184260 | A1 * | 7/2011 | Robinson et al. | 600/316 |

* cited by examiner

*Primary Examiner* — Kiet T Nguyen

(74) *Attorney, Agent, or Firm* — Joan Pennington

(57) ABSTRACT

A method and an ultrahigh-resolution spectrometer including a precision mechanical structure for positioning inelastic X-ray scattering optics are provided. The spectrometer includes an X-ray monochromator and an X-ray analyzer, each including X-ray optics of a collimating (C) crystal, a pair of dispersing (D) element crystals, anomalous transmission filter (F) and a wavelength (W) selector crystal. A respective precision mechanical structure is provided with the X-ray monochromator and the X-ray analyzer. The precision mechanical structure includes a base plate, such as an aluminum base plate; positioning stages for D-crystal alignment; positioning stages with an incline sensor for C/F/W-crystal alignment, and the positioning stages including flexure-based high-stiffness structure.

20 Claims, 9 Drawing Sheets

HIGH- STIFFNESS PRECISION LINEAR STAGE FOR D-CRYSTAL LINEAR ADJUSTMENT WITH VARIOUS LOAD MOMENT DIRECTIONS
600

800

(CENTRAL SET OF STAGES FOR C/F/W-CRYSTAL ALIGNMENT 306)

BASE STAGES FOR CDFDW MONOCHROMATOR 102 AND CDFDW ANALYZER 104
900

PRECISION MECHANICAL STRUCTURE OF AN ULTRA-HIGH-RESOLUTION SPECTROMETER FOR INELASTIC X-RAY SCATTERING INSTRUMENT

The United States Government has rights in this invention pursuant to Contract No. DE-AC02-06CH11357 between the United States Government and UChicago Argonne, LLC representing Argonne National Laboratory.

FIELD OF THE INVENTION

The present invention relates generally to inelastic X-ray scattering spectrometers, and more particularly, relates to a method and an ultrahigh-resolution spectrometer with a precision mechanical structure for positioning inelastic X-ray scattering optics.

DESCRIPTION OF THE RELATED ART

New inelastic X-ray scattering (IXS) spectrometers with improved energy and momentum resolutions are needed since many important scientific topics related to the high frequency dynamics of condensed matter require both a narrower and steeper resolution function and access to a broader dynamic range than what are currently available.

Current inelastic scattering probes are limited in both energy resolution and dynamic range. A need exists to meet challenging mechanical and optical requirements of an inelastic X-ray scattering (IXS) spectrometer for producing ultrahigh-resolution inelastic X-ray scattering spectroscopy data for various scientific applications.

It is desirable to provide an improved inelastic X-ray scattering (IXS) spectrometer with enhanced performance capability, for example, with an energy resolution of 0.1-0.5 meV and momentum resolution of 0.01-0.1 $nm^{-1}$.

It is desirable to provide an enhanced inelastic X-ray scattering (IXS) spectrometer with a precision mechanical structure for positioning inelastic X-ray scattering optics.

SUMMARY OF THE INVENTION

Principal aspects of the present invention are to provide a method and an ultrahigh-resolution spectrometer with a precision mechanical structure for positioning inelastic X-ray scattering optics. Other important aspects of the present invention are to provide such method and ultrahigh-resolution spectrometer with the precision mechanical structure substantially without negative effect and that overcome some of the disadvantages of prior art arrangements.

In brief, a method and an ultrahigh-resolution spectrometer including a precision mechanical structure for positioning inelastic X-ray scattering optics are provided. The spectrometer includes an X-ray monochromator and an X-ray analyzer, each including a collimating (C) crystal, a pair of dispersing (D) element crystals, anomalous transmission filter (F) and a wavelength (W) selector crystal. A respective precision mechanical structure is provided with the X-ray monochromator and the X-ray analyzer. The precision mechanical structure includes a base plate, such as an aluminum base plate; positioning stages for D-crystal alignment; and positioning stages with an incline sensor for C/F/W-crystal alignment, the positioning stages including flexure-based high-stiffness structure.

In accordance with features of the invention, the dispersing (D) element crystals include strain-free monolithic D-crystals. The dispersing (D) element crystals include ultrahigh-quality comb-style D-crystals.

In accordance with features of the invention, the respective precision mechanical structure simultaneously adjusts the respective dispersing (D) element crystal or D-crystal to a respective angle represented by $\theta_{D1}$ and $\theta_{D1}$. Each of the D-crystals is mounted in a holder, and multiple positioning stages, such as three stages are stacked together for each of the D-crystals including flexure-based high-stiffness positioning structure to control the dispersing (D) element crystal's pitch angle $\theta_D$ coarse and fine motion, linear fine positioning L, and the D-crystal's roll angle $\chi$ adjustment.

In accordance with features of the invention, the respective precision mechanical structure for each of the D-crystals is a multi-dimensional flexure-based high stiffness structure enabling a sub-microradian-level angular positioning stability with a large system orientation dynamic range. An over-constrained rotary weak-link mechanism of a compact PZT-driven rotary stage controls the dispersing (D) element crystal's angle $\theta_D$ fine and coarse positioning, for example, enables better than 0.002 arc sec positioning resolution in an 1.1 degree angular travel range.

In accordance with features of the invention, the collimating (C) crystal and wavelength (W) selector crystal include a central ultra-thin C/W crystal, such as a silicon crystal about 300 μm thick. The collimating (C) crystal, anomalous transmission filter (F) and wavelength (W) selector crystal performs collimation of the incident X-ray beam and performs wavelength-selection.

In accordance with features of the invention, the ultrahigh-resolution spectrometer with the precision mechanical structure for positioning inelastic X-ray scattering optics using a combined effect of angular dispersion and anomalous transmission of X-rays in Bragg reflection involving the CDFDW monochromator and the CDFDW analyzer provides spectral distributions of X-rays with shaped profiles with Gaussian-like, sharp tails and small bandwidth.

In accordance with features of the invention, the ultrahigh-resolution spectrometer with the precision mechanical structure for positioning inelastic X-ray scattering optics provides an energy resolution of, for example, 0.1-0.5 meV and momentum resolution of, for example, 0.01-0.1 $nm^{-1}$.

In accordance with features of the invention, the positioning stages with an incline sensor for C/W-crystal alignment include a base support, a thin film silicon C/F/W crystal holder, a picomotor actuator, a grating optical encoder, and flexure pivots. A diagnostic detector is provided with the positioning stages for C/F/W-crystal alignment.

In accordance with features of the invention, the incline sensor includes a microelectromechanical systems (MEMS) inclinometer.

In accordance with features of the invention, the positioning stages for D-crystal alignment include a base support, an angular flexure arm, a picomotor with rotary encoder, an angular flexure arm, and flexure pivots for D-crystal roll angle adjustment. The positioning stages include a high-stiffness precision linear stage for D-crystal linear positioning with various load moment directions including a base support, linear weak-link modules coupled to a carriage, a piezo motor actuator, and a grating optical encoder. The positioning stages for D-crystal alignment include a compact piezoelectric transducer (PZT)-driven sine bar rotary stage for D-crystal pitch angle coarse and fine motion control including a base support plate, weak-link modules coupled to a sine bar, a PZT with capacitance sensor and a picomotor with rotary encoder.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

In the following detailed description of embodiments of the invention, reference is made to the accompanying drawings, which illustrate example embodiments by which the invention may be practiced. It is to be understood that other embodiments may be utilized and structural changes may be made without departing from the scope of the invention.

The terminology used herein is for the purpose of describing particular embodiments only and is not intended to be limiting of the invention. As used herein, the singular forms “a”, “an” and “the” are intended to include the plural forms as well, unless the context clearly indicates otherwise. It will be further understood that the terms “comprises” and/or “comprising,” when used in this specification, specify the presence of stated features, integers, steps, operations, elements, and/or components, but do not preclude the presence or addition of one or more other features, integers, steps, operations, elements, components, and/or groups thereof.

In accordance with features of the invention, a method and an ultrahigh-resolution spectrometer including a precision mechanical structure for inelastic X-ray scattering optics are provided. The spectrometer X-ray optics include an X-ray monochromator and an X-ray analyzer, each including a collimating (C) crystal, a pair of dispersing (D) element crystals, an anomalous transmission filter (F) and a wavelength (W) selector crystal. A respective precision mechanical structure is provided with the X-ray monochromator and the X-ray analyzer defining the CDFDW X-ray optical configuration. The precision mechanical structure includes a base plate, such as an aluminum base plate; a pair of respective positioning stages for first D-crystal alignment and second D-crystal alignment; a central set of positioning stages with an incline sensor for C/F/W-crystal alignment; and a pair of rotary positioning actuators for alignment detectors.

Figure 1:
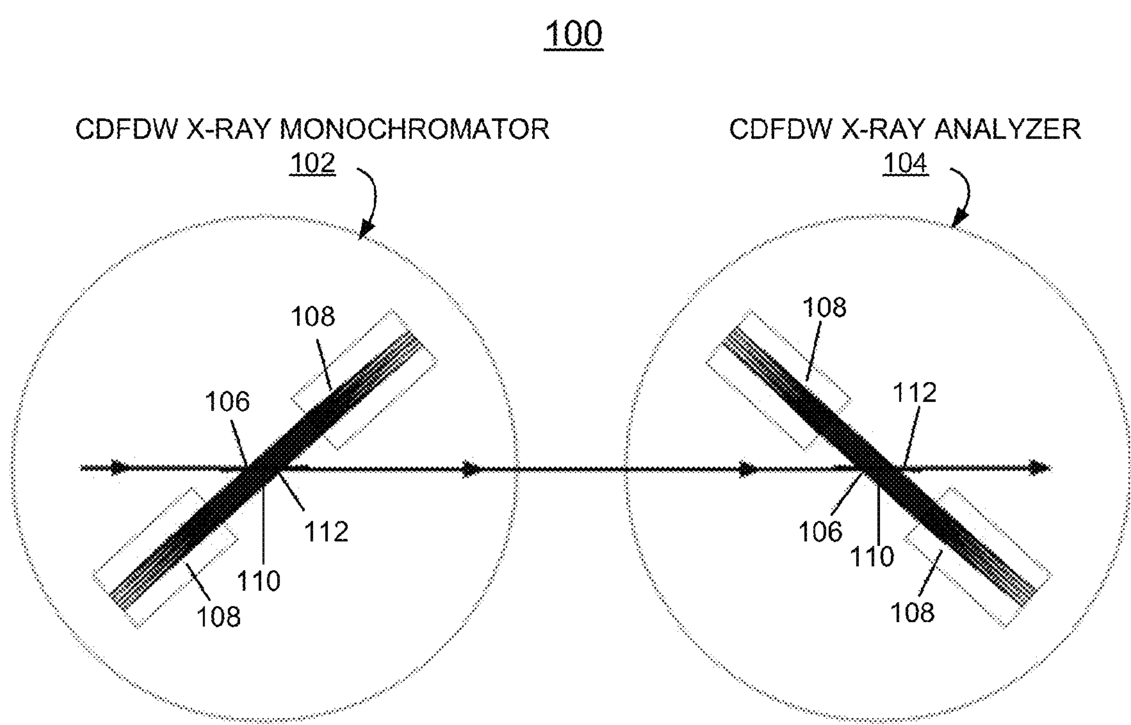
FIGS. 1 and 2 schematically illustrate example ultrahigh-resolution spectrometer with X-ray optics including an X-ray monochromator and an X-ray analyzer in accordance with a preferred embodiment.
Figure 2:
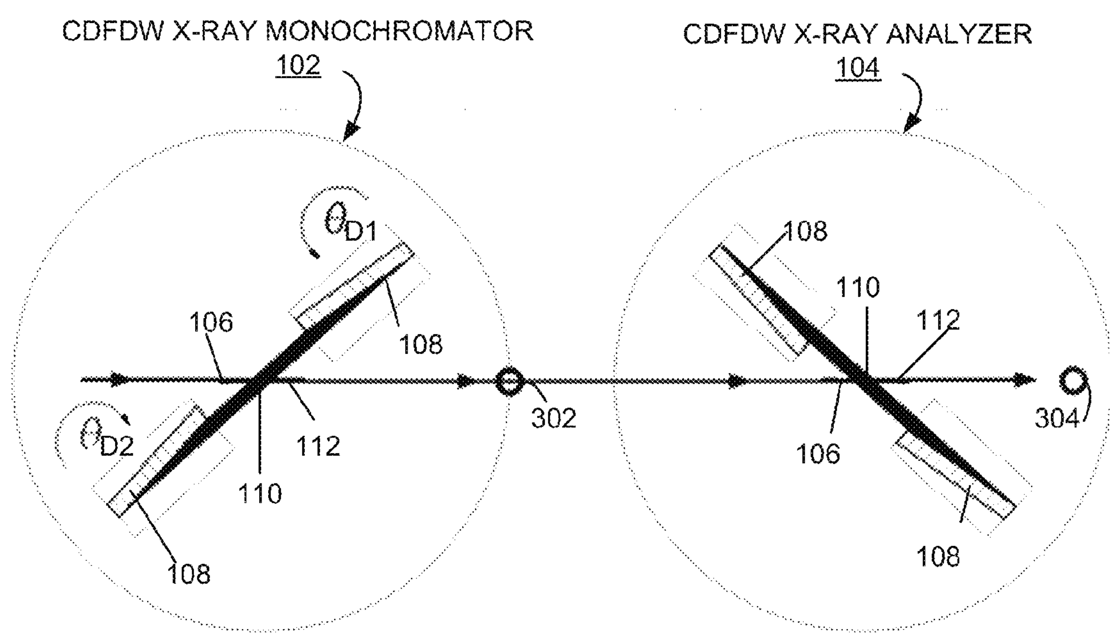

Having reference now to the drawings, in FIGS. 1 and 2, there is shown an example ultrahigh-resolution spectrometer including a precision mechanical structure for inelastic X-ray scattering generally designated by the reference character 100 in accordance with the preferred embodiment. The ultrahigh-resolution spectrometer 100 includes an X-ray monochromator generally designated by the reference character 102 and an X-ray analyzer generally designated by the reference character 104. Each of the X-ray monochromator 102 and the X-ray analyzer 104 includes a collimating (C) crystal 106, a pair of dispersing (D) element crystals 108, an anomalous transmission filter (F) 110 is provided between the collimating (C) crystal 106 and a wavelength (W) selector crystal 112.

In accordance with features of the invention, the ultrahigh-resolution spectrometer 100 using a combined effect of angular dispersion and anomalous transmission of X-rays in Bragg reflection involving the CDFDW monochromator 102 and the CDFDW analyzer 104 provides spectral distributions of X-rays with shaped profiles with Gaussian-like, sharp tails and small bandwidth.

Referring to FIG. 2, the respective dispersing (D) element crystals or D-crystals 108 are simultaneously adjusted to a respective grating angle represented by $\theta_{D1}$ and $\theta_{D2}$. A respective detector 302, 204 is provided with the CDFDW monochromator 102 and the CDFDW analyzer 104. The output intensity of the CDFDW monochromator 102 is measured with monitor detector 304, and as the monochromatic beam passed through the CDFDW analyzer 104 the spectral resolution function is measured with detector 304.

Each of the dispersing (D) element crystals 108 includes, for example, a strain-free monolithic D-crystal. The dispersing (D) element crystals 108 optionally include ultrahigh-quality comb-style D-crystals. Each respective collimating (C) crystal 106 and wavelength (W) selector crystal 112 of the X-ray monochromator 102 and the X-ray analyzer 104 include a central ultra-thin C/W crystal, such as a silicon crystal about 300 μm thick. The collimating (C) crystal 106, anomalous transmission filter (F) 110 and wavelength (W) selector crystal 112 performs collimation of the incident X-ray beam and performs wavelength-selection.

In accordance with features of the invention, a prototype of the novel ultrahigh-resolution inelastic x-ray scattering spectrometer 100 has been designed and tested at undulator-based beamline 30-ID, at the Advanced Photon Source (APS), Argonne National Laboratory. This state-of-the-art instrument 100 is designed to meet challenging mechanical and optical specifications for producing ultrahigh-resolution inelastic x-ray scattering spectroscopy data for various scientific applications. Preliminary test results of the prototype ultrahigh-resolution inelastic x-ray scattering spectrometer 100 show major advantage over existing arrangements. The prototype ultrahigh-resolution inelastic x-ray scattering spectrometer 100 includes a mechanical structure, such as a precisions mechanical structure 300 illustrated and described with respect to FIG. 3, providing compactness and special performance for structural stability in nanometer scale with kilograms-level load capacity and the capability to handle the load with various moment directions. The mechanical structure of the invention is a significant improvement for various instruments which need positioning resolution and stability in nanometer scale with multidimensional alignment capability and environmental control.

In accordance with features of the invention, the prototype of the novel ultrahigh-resolution inelastic x-ray scattering spectrometer 100 included strain-free monolithic D-crystals 108 that were manufactured at Argonne National Laboratory and characterized using x-ray topography. An energy scan of the CDFDW monochromator 102 around 9.13-keV was performed by a simultaneous change of the angles $\theta_{D1}$ and $\theta_{D2}$ of the dispersive elements (D-crystals) 108, output intensity of the monochromator was measured with monitor 302, and as the monochromatic beam passed through the analyzer the spectral resolution function was measured with detector 304. A 0.65-meV combined energy resolution of the monochromator-analyzer pair was demonstrated in the in-line configuration (FIG. 11), as well as sharp tails of the spectral distribution function. The tails were very steep, more than 100 times steeper than the tails of a Lorentzian distribution with the same FWHM.

Figure 3:
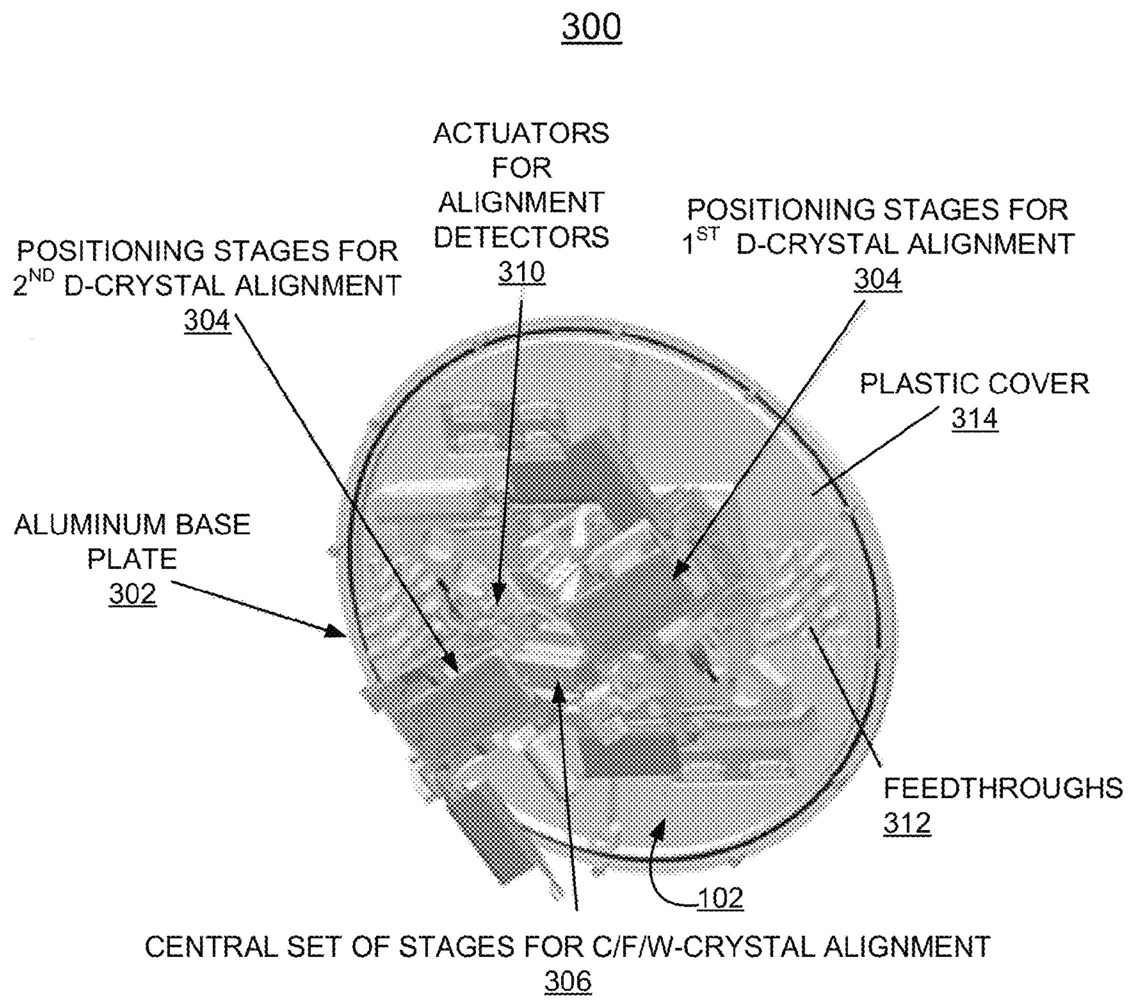
FIG. 3 illustrates a modular design of flexure stage groups of a precision mechanical structure for positioning inelastic X-ray scattering optics of the X-ray monochromator and X-ray analyzer of FIGS. 1 and 2 in accordance with preferred embodiments.
Figure 4:
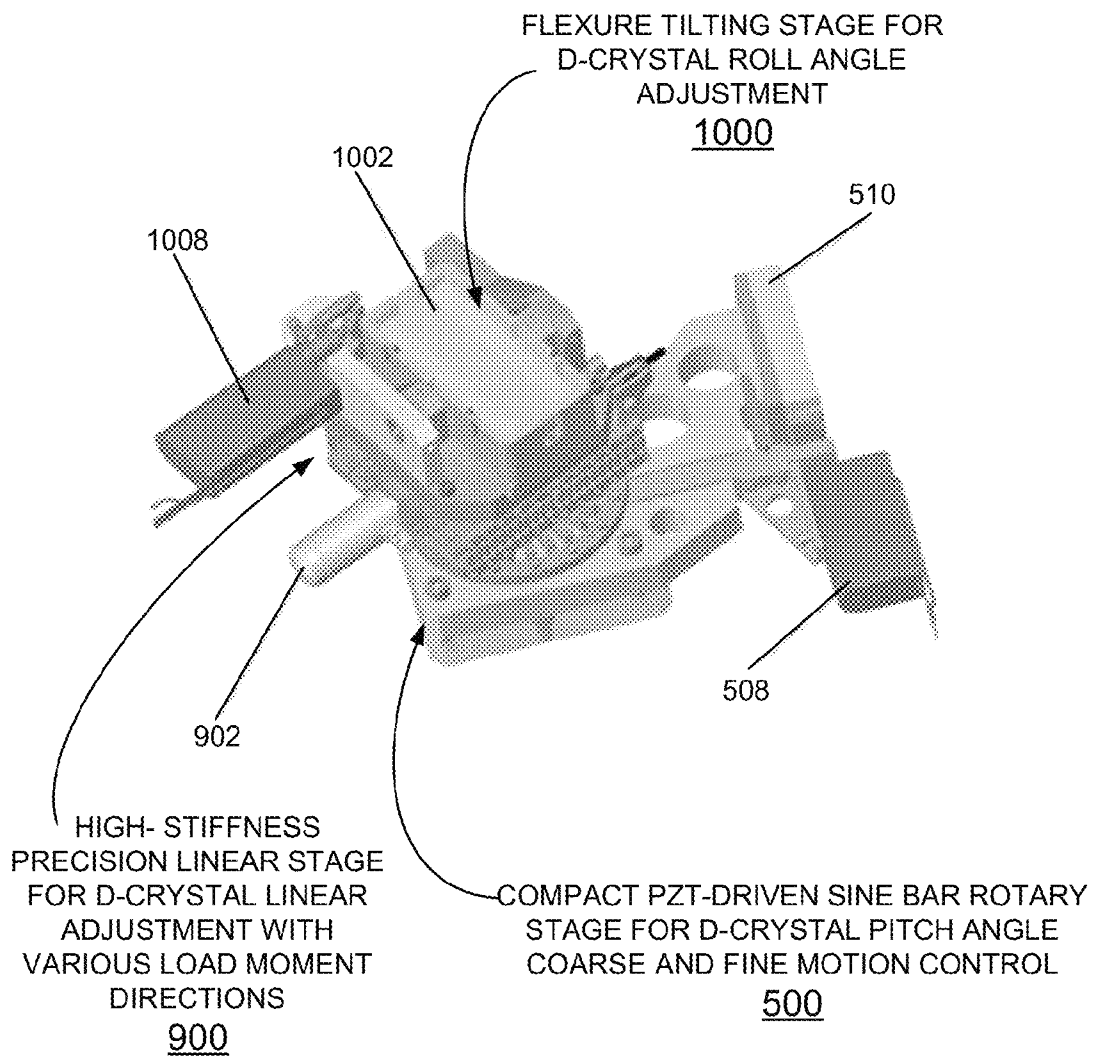
FIGS. 4 and 5 illustrate positioning stages of the precision mechanical structure of FIG. 3 for positioning of the dispersing (D) element crystals of the inelastic X-ray scattering optics of the X-ray monochromator and X-ray analyzer of FIGS. 1 and 2 in accordance with preferred embodiments.

Referring to FIG. 3, there is shown an example compact and modular design of flexure stage groups of a precision mechanical structure generally designated by the reference character 300 for positioning inelastic X-ray scattering optics of the CDFDW X-ray monochromator 102 and the CDFDW X-ray analyzer 104 in accordance with preferred embodiments. The precision mechanical structure 300 includes a base plate 302, such as an aluminum base plate; positioning stages for D-crystal alignment 304; and positioning stages with an incline sensor for C/F/W-crystal alignment 306. The positioning stages 302 and 304 including flexure-based high-stiffness structure. The precision mechanical structure 300 includes actuators for alignment detectors 310, feedthoughs 312, and a plastic cover 314, such as an acrylic cover for the CDFDW optics. The compact and modular design of the precision mechanical structure 300 enables achieving a milli-Kelvin-level temperature stability with a closed-loop feedback control (not shown).

In accordance with features of the invention, each of the stages for D-crystal alignment includes a respective holder for the D-crystals. Three flexure-based positioning stages are stacked together to control the dispersing element crystal's pitch angle $\theta_a$ coarse and fine motion, linear fine positioning L, and the crystal's roll angle $\chi$ adjustment. To achieve a better than 0.002 arc sec positioning resolution in an 1.1 degree angular travel range, a compact PZT-driven rotary stage has been designed for the dispersing element crystal's angle $\theta_a$ fine and coarse positioning using an overconstrained rotary weak-link mechanism.

In accordance with features of the invention, the precision mechanical structure 300 includes for each of the D-crystals a multi-dimensional flexure-based high stiffness structure, such as precision positioning stages 400 illustrated and described with respect to FIGS. 4, 5, 9 and 10, enabling a sub-microradian-level angular positioning stability with a large system orientation dynamic range. An overconstrained rotary weak-link mechanism of a compact PZT-driven rotary stage controls the dispersing (D) element crystal's angle $\theta_D$ fine and coarse positioning, for example, enables better than 0.002 arc sec positioning resolution in an 1.1 degree angular travel range.

Referring to FIGS. 4, 5, 6 and 7, there are shown example precision positioning stages generally designated by the reference character 400 for implementing the positioning stages for D-crystal alignment 304 of the precision mechanical structure 300 of FIG. 3 for positioning of the dispersing (D) element crystals of the inelastic X-ray scattering optics of the CDFDW X-ray monochromator 102 and the CDFDW X-ray analyzer 104 in accordance with preferred embodiments. The precision positioning stages 400 for positioning of the dispersing (D) element crystals (D-crystals) 108 include a stack of positioning stages including a compact PZT-driven sine bar rotary stage 500 for D-crystal pitch angle coarse and fine motion control, illustrated and described with respect to FIG. 5, a high-stiffness precision linear stage 600 for D-crystal linear adjustment with various load moment directions, illustrated and described with respect to FIG. 6, and a flexure tilting stage 700 for D-crystal roll angle adjustment, illustrated and described with respect to FIG. 7.

Figure 5:
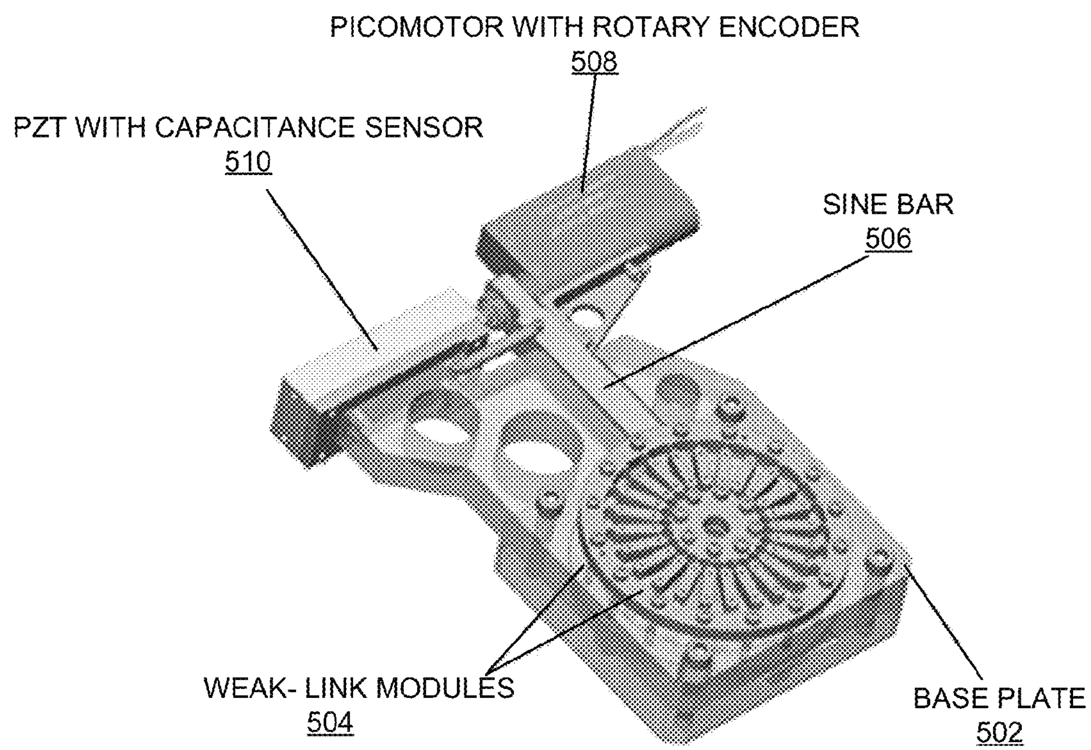

Referring to FIG. 5, the D-crystal positioning stages 400 include the lower compact PZT-driven sine bar rotary stage 500 for D-crystal pitch angle coarse and fine motion control. The compact PZT-driven sine bar rotary stage 500 includes a base support plate 502, weak-link modules 504 coupled to a sine bar 506, a picomotor with rotary encoder 508 and a PZT with capacitance sensor 510. The compact PZT-driven sine bar rotary stage 500 simultaneously adjusts the respective dispersing (D) element crystal or D-crystal to a respective angle represented by $\theta_{D1}$ and $\theta_{D1}$, as shown in FIG. 2.

Figure 6:
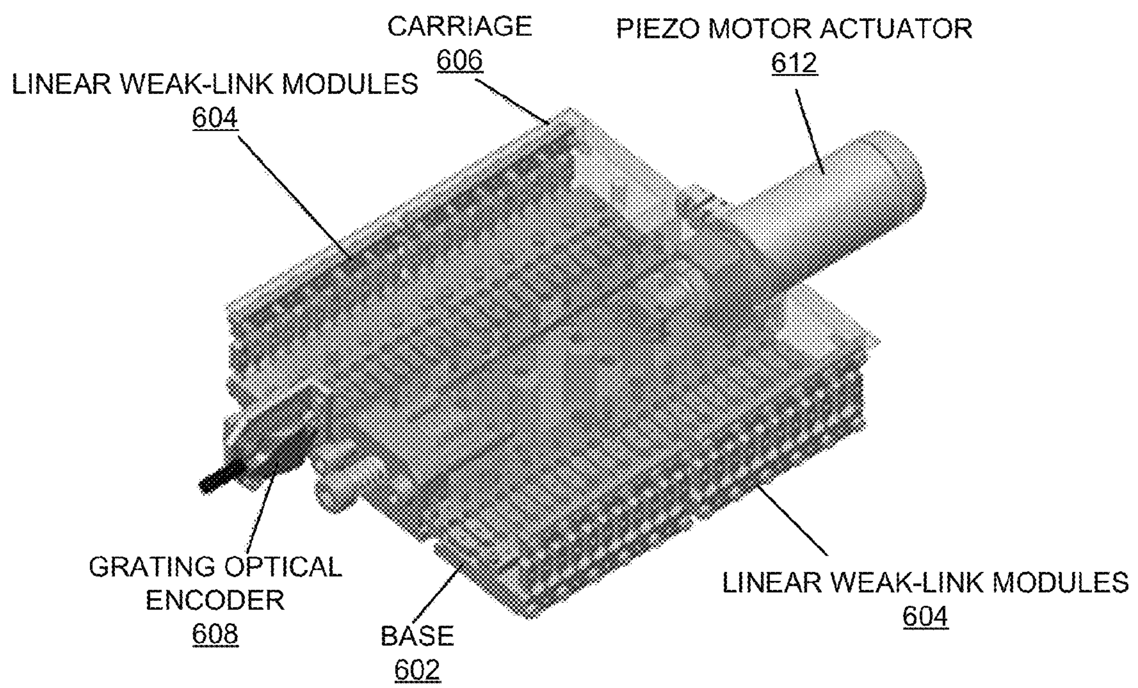
FIGS. 6 and 7 illustrate positioning stages of the precision mechanical structure of FIG. 3 for positioning of the dispersing (D) element crystals of the inelastic X-ray scattering optics of the X-ray monochromator and X-ray analyzer of FIGS. 1 and 2 in accordance with preferred embodiments.

Referring also to FIG. 6, the D-crystal positioning stages 400 include the central high-stiffness precision linear stage 600 for D-crystal linear positioning with various load moment directions. The high-stiffness precision linear stage 600 includes a base support 602, linear weak-link modules 604 coupled to a carriage 606, a grating optical encoder 608 and a piezo motor actuator 612.

An overconstrained weak-link mechanism is used for positioning of the dispersing (D) element crystals 108 implementing the weak-link modules 504 in accordance with preferred embodiments.

The rotary weak-link modules 504 and linear weak-link modules 604 provide enhanced structural stiffness and stability as compared to traditional kinematic linear spring mechanisms. The rotary weak-link modules 504 and linear weak-link modules 604 are implemented with planar-shape, high-stiffness, weak-link mechanisms.

U.S. Pat. Nos. 6,607,840, and 6,984,335 by Deming Shu, Thomas S. Toellner, E. Ercan Alp and assigned to the present assignee disclose redundantly constrained laminar structures as weak-link mechanisms and a novel method for manufacturing the redundantly constrained laminar structures as weak-link mechanisms. The method for producing the redundantly constrained laminar structures as weak-link mechanisms is carried out by lithographic techniques. A designed pattern is repeatedly chemically etched with a mask to produce a plurality of individual identical units. The units are stacked together to form the laminar structure and are secured together with fasteners. A high quality adhesive can be applied to the sides of the laminar structure to provide the mechanism equivalent to a single piece mechanism. The redundantly constrained laminar structures as weak-link mechanisms of the invention include a stack of a plurality of thin material structures. The stack of structures forming a laminar structure include multiple weak-link connections providing controllable movements in a plane of the layer and having a desired stiffness and stability. The plurality of thin material structures include predetermined locating-holes used with locating-pins to precisely stack the thin material structures together and are used to secure the stack together with fasteners.

U.S. Pat. No. 8,089,199 by Deming Shu and Jorg M. Maser and assigned to the present assignee discloses weak-link rotary mechanisms for implementing angular rotations with a defined angular travel range and positioning resolution, for example, with ten-degree-level travel range and ten-nanoradian-level positioning resolution. A weak-link rotary structure has a predetermined pattern for implementing angular rotations with repeatable and reliable angular travel range and positioning resolution including a plurality of connecting links radially extending from a central portion with a predefined angular separation between the connecting links;

each said connecting link having at least one pair of weak-link connections; alternate connecting links being coupled to a respective terminal, each said respective terminal being mounted to a connecting carriage; remaining other connecting links being coupled to a respective mounting portion of a mating part of the weak-link rotary structure.

The rotary weak-link modules 504 and linear weak-link modules 604 are implemented by redundantly overconstrained laminar structures as weak-link mechanisms and manufactured in accordance with the disclosures and teachings of the above identified U.S. Pat. Nos. 6,607,840, 6,984,335, and 8,089,199. The subject matter of the above identified U.S. Pat. Nos. 6,607,840, 6,984,335, and 8,089,199 are incorporated herein by reference.

Figure 7:
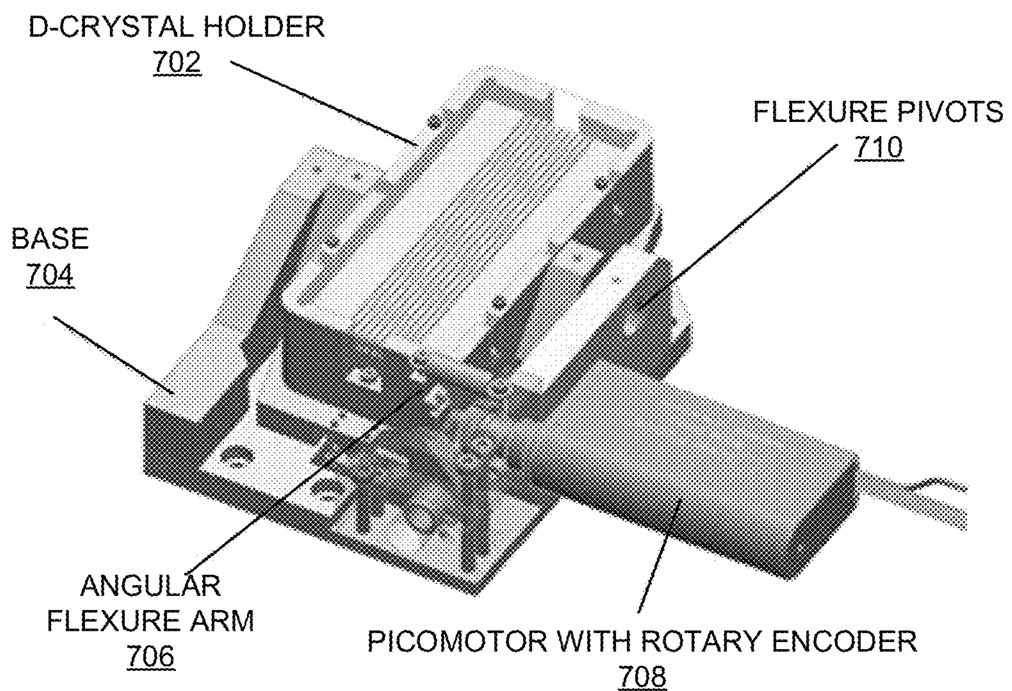

Referring to FIG. 7, the D-crystal positioning stages 400 include the upper tilting stage 700 for D-crystal roll angle adjustment. The tilting stage 700 for D-crystal roll angle adjustment includes a D-crystal holder 702, a base support member or base 704, an angular flexure arm 706, a picomotor with rotary encoder 708, and flexure pivots 710 for D-crystal roll angle adjustment.

Figure 8:
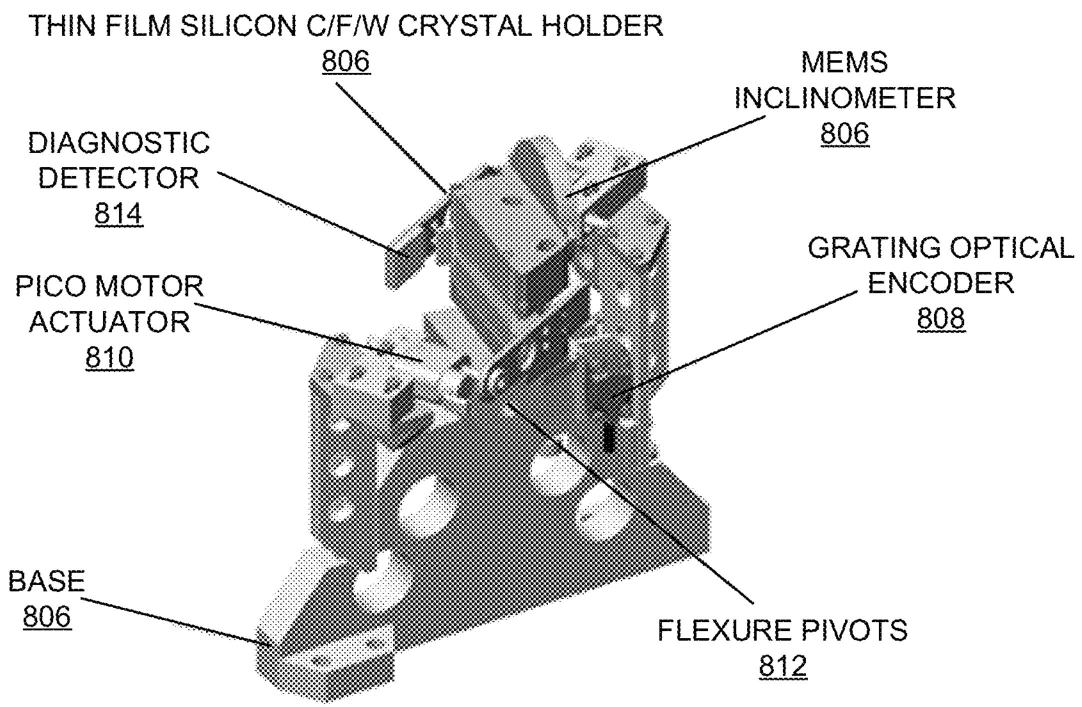
FIG. 8 illustrates a central set of positioning stages of the precision mechanical structure of FIG. 3 for positioning of the collimating (C) crystal and wavelength-selector (W) crystal alignment of the inelastic X-ray scattering optics of the X-ray monochromator and X-ray analyzer of FIGS. 1 and 2 in accordance with preferred embodiments.

Referring to FIG. 8, there are shown example precision positioning stages generally designated by the reference character 800 for implementing the central set of positioning stages 306 of the precision mechanical structure 300 of FIG. 3 for positioning of the C/F/W-crystal alignment of the inelastic X-ray scattering optics of the CDFDW X-ray monochromator 102 and the CDFDW X-ray analyzer 104 in accordance with preferred embodiments. The precision positioning stages 800 for positioning of the C/F/W-crystal alignment include a base support 802, a thin film silicon C/F/W crystal holder 804, a picomotor actuator 806, a grating optical encoder 808, and flexure pivots 810. An incline sensor 812 provided with the positioning stages 800 includes a microelectromechanical systems (MEMS) inclinometer. A diagnostic detector 814 is provided with the positioning stages 800 for C/F/W-crystal alignment.

Figure 9:
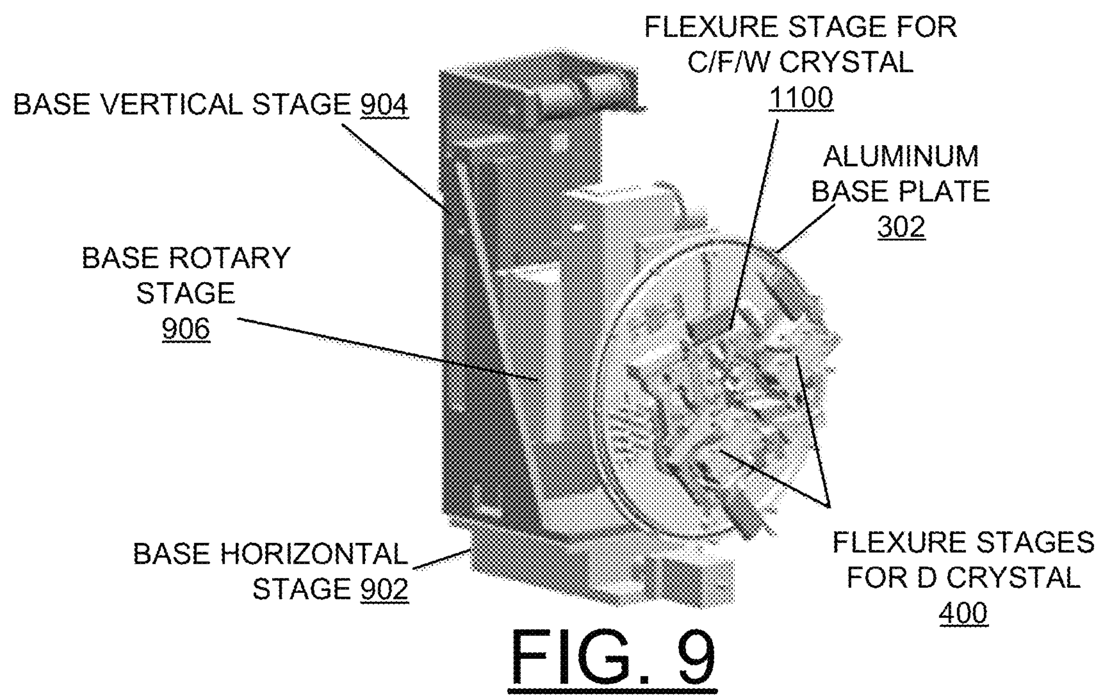
FIG. 9 illustrates example base positioning stages of the X-ray monochromator and X-ray analyzer of FIGS. 1 and 2 in accordance with preferred embodiments.

Referring to FIG. 9, there are shown example base positioning stages generally designated by the reference character 900 respectively provided with each of the CDFDW X-ray monochromator 102 and the CDFDW X-ray analyzer 104 in accordance with preferred embodiments. The base positioning stages 900 include a base horizontal stage 902, a base vertical stage 904 and a base rotary stage 906 for the alignment of all of the inelastic X-ray scattering optics of the CDFDW X-ray monochromator 102 and the CDFDW X-ray analyzer 104 in accordance with preferred embodiments.

While the present invention has been described with reference to the details of the embodiments of the invention shown in the drawing, these details are not intended to limit the scope of the invention as claimed in the appended claims.

What is claimed is:

1. An ultrahigh-resolution spectrometer with a precision mechanical structure for positioning inelastic X-ray scattering optics comprising:

an X-ray monochromator;

an X-ray analyzer coupled to said X-ray monochromator;

each of said X-ray monochromator and said X-ray analyzer including X-ray optics of a collimating (C) crystal, a pair of dispersing (D) element crystals, an anomalous transmission filter (F), and a wavelength (W) selector crystal;

each of said X-ray monochromator and said X-ray analyzer including a respective precision mechanical structure; and each of said respective precision mechanical structure including a base plate; positioning stages for D-crystal alignment; positioning stages including an incline sensor for C/F/W-crystal alignment; and said positioning stages including flexure-based high-stiffness structure.

2. The ultrahigh-resolution spectrometer as recited in claim 1 wherein said dispersing (D) element crystals includes a selected one of strain-free monolithic D-crystals and comb-style D-crystals.

3. The ultrahigh-resolution spectrometer as recited in claim 1 wherein said collimating (C) crystal, said anomalous transmission filter (F), and said wavelength (W) selector crystal perform collimation and wavelength-selection of an incident X-ray beam; and said collimating (C) crystal and wavelength (W) selector crystal include a silicon crystal about 300 μm thick.

4. The ultrahigh-resolution spectrometer as recited in claim 1 wherein base plate includes an aluminum base plate supporting said positioning stages for D-crystal alignment and said positioning stages including an incline sensor for C/F/W-crystal alignment.

5. The ultrahigh-resolution spectrometer as recited in claim 1 wherein said positioning stages for D-crystal alignment include flexure-based high-stiffness positioning structure to control dispersing (D) element crystal's pitch angle $\theta_D$ coarse and fine motion, linear fine positioning L, and dispersing (D) element crystal's roll angle $\chi$ adjustment.

6. The ultrahigh-resolution spectrometer as recited in claim 1 wherein said positioning stages for D-crystal alignment include a rotary stage for D-crystal pitch alignment; said rotary stage including weak-link modules.

7. The ultrahigh-resolution spectrometer as recited in claim 1 wherein said positioning stages for D-crystal alignment include a high stiffness linear stage for D-crystal linear adjustment; said linear stage including linear weak-link modules.

8. The ultrahigh-resolution spectrometer as recited in claim 1 wherein said positioning stages for D-crystal alignment include a flexure tilting stage for D-crystal roll angle adjustment; said flexure tilting stage including a D-crystal holder.

9. The ultrahigh-resolution spectrometer as recited in claim 1 wherein said positioning stages for D-crystal alignment are stacked together for each of the D-crystals including flexure-based high-stiffness positioning structure to control the dispersing (D) element crystal's pitch angle $\theta_D$ coarse and fine motion, linear fine positioning L, and the D-crystal's roll angle $\chi$ adjustment.

10. The ultrahigh-resolution spectrometer as recited in claim 1 wherein said positioning stages for D-crystal alignment include a stack of precision positioning stages including a lower PZT-driven sine bar rotary stage for pitch angle coarse and fine motion control alignment; a central high stiffness linear stage for D-crystal linear adjustment; and an upper flexure tilting stage for D-crystal roll angle adjustment.

11. The ultrahigh-resolution spectrometer as recited in claim 1 wherein said positioning stages including said incline sensor for C/F/W-crystal alignment include a thin film silicon C/F/W crystal holder.

12. The ultrahigh-resolution spectrometer as recited in claim 1 wherein said incline sensor includes a microelectromechanical systems (MEMS) inclinometer.

13. The ultrahigh-resolution spectrometer as recited in claim 1 wherein said positioning stages including said incline sensor for C/F/W-crystal alignment include a base support, a thin film silicon C/F/W crystal holder, a picomotor actuator, a grating optical encoder, and flexure pivots.

14. The ultrahigh-resolution spectrometer as recited in claim 1 wherein said ultrahigh-resolution spectrometer with the precision mechanical structure for positioning inelastic X-ray scattering optics provides spectral distributions of X-rays with shaped profiles with Gaussian-like, sharp tails and small bandwidth.

15. The ultrahigh-resolution spectrometer as recited in claim 1 wherein said ultrahigh-resolution spectrometer with the precision mechanical structure for positioning inelastic X-ray scattering optics provides enhanced performance capability.

16. The ultrahigh-resolution spectrometer as recited in claim 15 wherein said enhanced performance capability includes an energy resolution in a range of approximately 0.1-0.5 meV and momentum resolution in a range of approximately 0.01-0.1 $nm^{-1}$.

17. The ultrahigh-resolution spectrometer as recited in claim 1 wherein each of said X-ray monochromator and said X-ray analyzer includes a compact structure having structural stability in a nanometer scale.

18. A method for implementing an ultrahigh-resolution spectrometer with a precision mechanical structure for positioning inelastic X-ray scattering optics comprising:

providing an X-ray monochromator;

providing an X-ray analyzer coupled to said X-ray monochromator;

providing each of said X-ray monochromator and said X-ray analyzer with X-ray optics including a collimating (C) crystal, a pair of dispersing (D) element crystals, an anomalous transmission filter (F), and a wavelength (W) selector crystal;

providing a respective precision mechanical structure for each of said X-ray monochromator and said X-ray analyzer including providing a base plate; and providing positioning stages for D-crystal alignment and providing positioning stages including an incline sensor for C/F/W-crystal alignment; and said positioning stages being mounted on said base plate and said positioning stages including flexure-based high-stiffness structure.

19. The method as recited in claim 18 wherein providing positioning stages for D-crystal alignment includes providing flexure-based high-stiffness positioning structure to control the dispersing (D) element crystal's pitch angle $\theta_D$ coarse and fine motion, linear fine positioning L, and the D-crystal's roll angle $\chi$ adjustment.

20. The method as recited in claim 18 wherein providing positioning stages for D-crystal alignment includes providing a stack of positioning stages including a lower PZT-driven sine bar rotary stage for pitch angle coarse and fine motion control alignment; a central high stiffness linear stage for D-crystal linear adjustment; and an upper flexure tilting stage for D-crystal roll angle adjustment.

* * * * *